(12) United States Patent
L'Alloret et al.

(10) Patent No.: US 10,773,106 B2
(45) Date of Patent: Sep. 15, 2020

(54) OIL-IN-WATER EMULSION CONTAINING AN AMPHIPHILIC POLYMER

(75) Inventors: Florence L'Alloret, Paris (FR); Lydie Bressy, Paris (FR)

(73) Assignee: L'OREAL, Paris (FR)

( * ) Notice: Subject to any disclaimer, the term of this patent is extended or adjusted under 35 U.S.C. 154(b) by 1174 days.

(21) Appl. No.: 12/173,126

(22) Filed: Jul. 15, 2008

(65) Prior Publication Data

US 2009/0022680 A1    Jan. 22, 2009

Related U.S. Application Data

(60) Provisional application No. 60/951,964, filed on Jul. 26, 2007.

(30) Foreign Application Priority Data

Jul. 20, 2007   (FR) ..................... 07 56636

(51) Int. Cl.
| | | |
|---|---|---|
| *A61Q 19/00* | (2006.01) | |
| *A61K 8/06* | (2006.01) | |
| *A61K 8/39* | (2006.01) | |
| *A61K 8/81* | (2006.01) | |
| *A61K 8/86* | (2006.01) | |
| *A61K 8/37* | (2006.01) | |

(52) U.S. Cl.
CPC ............... *A61Q 19/00* (2013.01); *A61K 8/06* (2013.01); *A61K 8/062* (2013.01); *A61K 8/375* (2013.01); *A61K 8/39* (2013.01); *A61K 8/8158* (2013.01); *A61K 8/86* (2013.01)

(58) Field of Classification Search
CPC .......... A61Q 19/00; A61K 8/06; A61K 8/062; A61K 8/04; A61K 8/37; A61K 8/375; A61K 8/8158
See application file for complete search history.

(56) References Cited

U.S. PATENT DOCUMENTS

| | | | | |
|---|---|---|---|---|
| 6,645,476 | B1 * | 11/2003 | Morschhauser et al. | 424/70.1 |
| 6,905,674 | B2 * | 6/2005 | L'Alloret | 424/59 |
| 6,955,803 | B2 * | 10/2005 | Boutelet et al. | 424/59 |
| 7,045,120 | B2 * | 5/2006 | Boutelet et al. | 424/59 |
| 7,615,586 | B2 * | 11/2009 | Moreno | 524/211 |
| 7,879,345 | B2 * | 2/2011 | Aubrun-Sonneville et al. | 424/401 |
| 2005/0287088 | A1 * | 12/2005 | Guiramand | A61K 8/062 424/59 |

FOREIGN PATENT DOCUMENTS

| | | |
|---|---|---|
| EP | 1 069 142 | 1/2001 |
| EP | 1 302 190 | 4/2003 |
| FR | 2 843 695 | 2/2004 |
| FR | 2 853 527 | 10/2004 |
| FR | 2 853 544 | 10/2004 |

* cited by examiner

*Primary Examiner* — Lakshmi S Channavajjala
(74) *Attorney, Agent, or Firm* — Oblon, McClelland, Maier & Neustadt, L.L.P.

(57) ABSTRACT

A composition for topical application, in the form of an oil-in-water emulsion, containing at least one nonionic emulsifier with a melting point of less than 45° C. and at least one 2-acrylamido-2-methylpropanesulfonic acid polymer. The composition shows very good stability.

4 Claims, No Drawings

OIL-IN-WATER EMULSION CONTAINING AN AMPHIPHILIC POLYMER

REFERENCE TO PRIOR APPLICATIONS

This application claims priority to U.S. provisional application 60/951,964 filed Jul. 26, 2007, and to French patent application 0756636 filed Jul. 20, 2007, both incorporated herein by reference.

FIELD OF THE INVENTION

The present patent application relates to a composition in the form of an oil-in-water emulsion containing at least one particular amphiphilic polymer and a particular nonionic emulsifier, and to the use of the composition, especially for caring for, removing makeup from and/or cleansing a keratin material such as body or facial skin, the hair, the lips and/or the eyes.

Additional aspects and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous dispersing continuous phase and an oily dispersed discontinuous phase, or of an emulsion of the water-in-oil (W/O) type consisting of an oily dispersing continuous phase and an aqueous dispersed discontinuous phase. O/W emulsions are the ones most sought in the cosmetics field, since they comprise an aqueous phase as external phase, which gives them, when applied to the skin, a fresher, less greasy and lighter feel than W/O emulsions.

Standard O/W emulsions are generally stabilized with amphiphilic molecules of low molar mass (<5000 g/mol), such as emulsifying surfactants of the alkylglycerol or alkylpolyoxyethylene type. However, these surfactants, when they are in a certain amount, have the drawback of inducing a waxy, heavy feel. In addition, it is sought to have available compositions containing the smallest possible amount of surfactants, since they are occasionally poorly tolerated by sensitive skin.

Moreover, it is known practice to replace surfactants with modified carboxyvinyl polymers, i.e. polymers comprising a hydrophobic portion constituted by a fatty chain, such as copolymers of $C_{10}$-$C_{30}$-alkyl acrylate and of acrylic or methacrylic acid, for instance the products sold under the name Pemulen by the company Noveon. However, these polymers lead to emulsions comprising large-sized drops (~10-15 µm), which are difficult to stabilize when it is desired to obtain fluid textures, this resulting in the phenomenon of creaming of the emulsion. These copolymers are moreover pH-sensitive, and must be formulated at a pH above 6 to benefit from their gelling and emulsifying properties.

Moreover, it is known practice from document EP-A-1 069 142 to use amphiphilic polymers derived from 2-acrylamido-2-methylpropanesulfonic acid (AMPS), these polymers possibly being used as thickeners, emulsifiers, dispersants and suspending agents, especially in the cosmetics field. However, the polymers illustrated in the document do not allow the production of O/W emulsions which simultaneously have cosmetic properties that are pleasant for the user and which are very stable and easy to prepare.

Patent application EP-1 302 190 describes makeup-removing emulsions stabilized with an AMPS-based amphiphilic polymer; Example 1 corresponds to an emulsion comprising 1% emulsifying polymer and 20% makeup-removing fatty phase. During application to the skin, the emulsion breaks and leads to a non-uniform deposit corresponding to "quick-break" textures. Although very advantageous for removing makeup, this behaviour is not favourable to the uniform deposition of active agents on the surface of the skin and does not lead to smooth, fondant textures on the surface of the skin.

Document FR-2 843 695 describes O/W emulsions containing an amphiphilic polymer of non-crosslinked AMPS and an oil content of greater than 40% by weight. However such an amount of oily phase leads to a greasy and shiny effect during application to the skin, which the user may find unacceptable.

Moreover, document FR-2 853 527 relates to O/W emulsions containing a non-crosslinked AMPS-based amphiphilic polymer bearing $C_6$-$C_{15}$ alkyl chains and a lipophilic emulsifier, and describes compositions whose texture usually remains fluid. However, these polymers cannot afford textures of thicker consistency such as creams other than by using a large amount of oily phase or by introducing an additional hydrophilic gelling agent into the aqueous phase. Moreover, in the examples, the amount of polymer is at least 0.8%.

Document FR-2 853 544 describes O/W emulsions containing a non-crosslinked AMPS-based amphiphilic polymer, comprising specific proportions of hydrophobic and hydrophilic portions depending on the carbon number of the alkyl chain. These emulsions are in the form of fluid textures, and they contain a large amount of polymer. Comparative Example 2 of the patent application comprises a high polymer content (1.75%), which, admittedly, leads to a stable emulsion without the addition of surfactants, but its texture is gelled and quivery, is cosmetically unattractive and is difficult to take up by finger.

OBJECTS OF THE INVENTION

Thus, there is still a need to prepare O/W emulsions that overcome the difficulties of the prior art, i.e. that have good cosmetic qualities (pleasant feel on application), good stability and very varied textures ranging from a sprayable fluid to a thick cream, while at the same time having limited amounts of oily phase, polymer and surfactants.

SUMMARY OF THE INVENTION

The inventors have discovered, unexpectedly, that the combination in specific proportions of one or more particular non-crosslinked AMPS amphiphilic polymers and one or more nonionic emulsifiers allows emulsions that overcome the difficulties of the prior art to be prepared. Stable oil-inwater emulsions having noteworthy sensory qualities with a glidant and non-tacky feel, and which may equally be in the form of fluid products or in the form of thick creams, may thus be obtained according to the invention.

DETAILED DESCRIPTION OF THE PREFERRED EMBODIMENTS

Thus, the present invention relates in one embodiment to a composition preferably suitable for topical application, for example in the form of an oil-in-water emulsion comprising an oily phase dispersed in an aqueous phase, wherein it contains (a) one or more nonionic emulsifiers with a melting point of less than 45° C., and (b) one or more non-crosslinked polymers comprising (A) 80 mol % to 99 mol % of 2-acrylamido-2-methylpropanesulfonic acid units of formula (I):

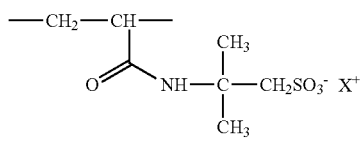

in which $X^+$ is a proton, an alkali metal cation, an alkaline-earth metal cation or an ammonium ion;
and (B) 1 mol % to 20 mol % of units of formula (II) below:

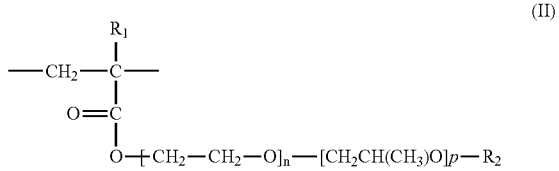

in which n and p, independently of each other, denote a number ranging from 0 to 30 and preferably from 1 to 25, with the proviso that n+p is less than or equal to 30, preferably less than 25 and better still less than 20; $R_1$ denotes a hydrogen atom or a linear or branched $C_1$-$C_6$ alkyl radical (preferably methyl) and $R_2$ denotes a linear or branched alkyl radical containing from 16 to 30 carbon atoms and preferably from 16 to 25 carbon atoms,
the amount of polymer(s) (b) being less than or equal to 0.6% by weight relative to the total weight of the composition, and the weight ratio between the amount of polymer(s) (b) and the amount of emulsifier(s) (a) ranging from 0.7 to 1.3,
and in that the oily phase is present in an amount of less than 40% by weight relative to the total weight of the composition.

In the present invention, the amount of oily phase does not include the amount of nonionic emulsifiers used according to the invention.

The mole proportion of hydrophobic monomer of formula (II) corresponds to the mole percentage of side chain of unit (II) relative to the sum of the units (I) and (II).

The term "topical application" means herein an external application to keratin materials, which are especially the skin, the scalp, the eyelashes, the eyebrows, the nails, mucous membranes and the hair.

Since the composition according to the invention is preferably intended for topical application, it contains a physiologically acceptable medium, i.e. a medium that is compatible with the skin, mucous membranes, the hair and the scalp.

The composition according to the invention has the advantage of having good harmlessness and good cosmetic properties, i.e. a uniform and pleasant texture on application. In addition, it is very stable over time. The term "stable" refers to a composition which, after at least one month or more of storage, at any temperature between 4° C. and 45° C., shows no macroscopic change in colour, odour or viscosity, or any variation in pH, or any change in microscopic appearance.

The polymers used in the composition of the invention have the advantage of allowing the dispersion of oils of any nature, which may equally be oils constituted by triglycerides or alkanes, esters, silicones, sunscreens or perfluoro oils, either alone or as mixtures. In addition, they have the advantage of being sparingly sensitive to pH variations for values of between 4 and 8, which are the usual values for cosmetic compositions.

The mean size of the oil drops in the dispersions obtained is generally preferably between 100 nm and 10 μm.

The viscosity of the dispersions obtained may range from very fluid (spray) to very viscous (cream) and is adjusted as a function of the content of introduced polymer, of the content of emulsified oily phase and of the emulsification process used, depending on whether it is desired to obtain a micron-sized emulsion (mean diameter of the oil drops of greater than or equal to 1 μm) or a submicron-sized emulsion (mean diameter of the oil drops of less than or equal to 1 μm). The composition of the invention thus has a viscosity that may vary widely according to the desired final aim. Thus, its viscosity may range, for example, from 0.01 Pa·s to 100 Pa·s at a temperature of 25° C., the viscosity being measured using a Rheomat 180 viscometer for a spindle spin speed of 200 rpm (revolutions per minute).

The emulsification processes may be performed with machines of paddle, impeller or rotor-stator type, and also by high-pressure homogenization (HPH).

To obtain stable emulsions with a low content of polymer (oil/polymer ratio >25), it is possible to do the dispersion in concentrated phase and then to dilute the dispersion with the rest of the aqueous phase.

It is also possible, via HPH (between 50 and 800 bar), to obtain stable dispersions with drop sizes that may be as low as 100 nm.

Polymers

The amphiphilic polymers used in the composition of the invention are water-soluble or water-dispersible. The expression "water-soluble or water-dispersible polymer" means a polymer which, when introduced into water at a concentration equal to 1% by weight, gives a macroscopically homogeneous solution whose light transmittance, at a wavelength equal to 500 nm, through a sample 1 cm thick, is at least 10%, which corresponds to an absorbance [abs=−log(transmittance)] of less than 1.5.

They are amphiphilic polymers, i.e. polymers containing a hydrophilic chain and comprising one or more hydrophobic units.

The polymers in accordance with the invention generally have a weight-average molar mass ranging from 50 000 to 10 000 000, more preferentially from 100 000 to 8 000 000 and even more preferentially from 200 000 to 3 000 000.

The polymers in accordance with the invention are preferentially partially or totally neutralized with a mineral base, for instance sodium hydroxide, potassium hydroxide or aqueous ammonia, or with an organic base such as monoethanolamine, diethanolamine, triethanolamine, aminomethylpropanediol, N-methylglucamine, or basic amino acids, for instance arginine and lysine, and mixtures thereof.

The polymers used according to the invention may be obtained according to the standard free-radical polymerization processes in the presence of one or more initiators such as, for example, azobisisobutyronitrile (AIBN), azobisdimethylvaleronitrile, 2,2-azobis[2-amidinopropane] hydrochloride (ABAH), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The polymers are obtained preferably by free-radical polymerization in tert-butanol medium in which they precipitate. Using polymerization in tert-butanol, it is possible to obtain a size distribution of the polymer particles that is particularly favourable for its uses.

The polymerization reaction may be performed at a temperature of between 0 and 150° C., preferably between 20 and 100° C., either at atmospheric pressure or under reduced pressure. It may also be performed under inert atmosphere, and preferably under nitrogen.

According to one preferred embodiment, the polymer used according to the invention is a polymer comprising, as unit of formula (II), a unit in which p=0, i.e. the unit of formula (II) is free of oxypropylene groups and comprises only oxyethylene units, and this unit preferably has the formula (III) indicated below:

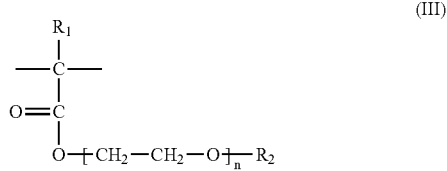

(III)

in which n denotes a number of moles and ranges from 1 to 30 and preferably from 6 to 25; $R_1$ denotes a linear or branched $C_1$-$C_6$ alkyl radical, preferably a methyl radical, and $R_2$ denotes a linear or branched alkyl radical containing from 16 to 30 carbon atoms and preferably from 16 to 25 carbon atoms, preferably a linear alkyl radical.

According to one preferred embodiment of the invention, in formula (II), p=0; $R_1$ is a methyl radical; n is an integer ranging from 6 to 25 and $R_2$ is a linear $C_{16}$-$C_{25}$ alkyl radical.

It is thus possible to use the polymers prepared from 2-acrylamido-2-methylpropanesulfonic acid (AMPS) or a salt thereof, especially the sodium or ammonium salt, with an ester of acrylic or methacrylic acid and:
  of a $C_{16}$-$C_{18}$ alcohol oxyethylenated with 8 mol of ethylene oxide (Genapol T-080 from the company Clariant),
  of a $C_{16}$-$C_{18}$ alcohol oxyethylenated with 11 mol of ethylene oxide (Genapol T-110 from the company Clariant),
  of a $C_{16}$-$C_{18}$ alcohol oxyethylenated with 15 mol of ethylene oxide (Genapol T-150 from the company Clariant),
  of a $C_{16}$-$C_{18}$ alcohol oxyethylenated with 20 mol of ethylene oxide (Genapol T-200 from the company Clariant),
  of a $C_{16}$-$C_{18}$ alcohol oxyethylenated with 25 mol of ethylene oxide (Genapol T-250 from the company Clariant),
  of a $C_{18}$-$C_{22}$ alcohol oxyethylenated with 25 mol of ethylene oxide,
  of a $C_{16}$-$C_{18}$ isoalcohol oxyethylenated with 25 mol of ethylene oxide.

According to one preferred embodiment, the polymer used according to the invention is a copolymer of AMPS and of a $C_{16}$-$C_{18}$ alkyl methacrylate comprising from 6 to 25 mol of ethylene oxide, this copolymer being obtained from AMPS and methacrylic acid or a methacrylic acid salt and from an oxyethylenated $C_{16}$-$C_{18}$ alcohol comprising 6 to 25 mol of ethylene oxide.

According to an even more preferred embodiment of the invention, the polymer used according to the invention is a copolymer of AMPS and of a $C_{16}$-$C_{18}$ alkyl methacrylate comprising from 6 to 10 mol of ethylene oxide, the mole proportion of $C_{16}$-$C_{18}$ alkyl methacrylate units (units (II)) of which ranges from 2% to 15% and better still from 5% to 10%. It is more particularly a copolymer of AMPS and of methacrylic acid or a methacrylic acid salt and of oxyethylenated cetearyl alcohol (Genapol T-080) comprising a mole proportion of alkyl methacrylate units of 7.35%.

A preferred polymer according to the invention that may be mentioned in particular is the copolymer of AMPS and of the ammonium salt of methacrylic acid and of oxyethylenated cetearyl alcohol comprising 8 mol of ethylene oxide (Genapol T-080 methacrylate) and comprising a mole proportion of alkyl methacrylate units of 7.35%, sold under the name Aristoflex SNC by the company Clariant (INCI name: Ammonium acryloyldimethyltaurate/Steareth-8 methacrylate copolymer).

The amount of AMPS polymer(s) as defined above is less than or equal to 0.6% by weight relative to the total weight of the composition. The amount (as active material) of AMPS polymer(s) in the composition of the invention may range, for example, as active material, from 0.01% to 0.6% by weight, preferably from 0.05% to 0.5% by weight and better still from 0.1% to 0.5% by weight relative to the total weight of the composition.

The weight ratio of the amount of polymer(s) (b) to the amount of emulsifier(s) (a) ranges from 0.7 to 1.3 and preferably ranges from 0.9 to 1.1, including all values and subranges between these stated values as if written out.

Emulsifiers

The composition according to the invention contains one or more nonionic emulsifiers with a melting point of less than 45° C. The term "with a melting point of less than 45° C." refers to nonionic emulsifiers that are liquid at a temperature below 45° C.

The amount (as active material) of emulsifier(s) may range, for example, from 0.007% to 0.78% by weight, preferably from 0.035% to 0.65% by weight and better still from 0.14% to 0.65% by weight relative to the total weight of the composition.

The emulsifiers may be chosen in particular from fatty acid esters of polyols, including those comprising at least one oxyethylene unit; fatty alkyl ethers of polyols; fatty acid esters of sorbitol, including those comprising at least one oxyethylene unit; fatty alkyl ethers of sorbitol; monoalkyl or polyalkyl esters or monoalkyl or polyalkyl ethers of sugars; alkoxylated alkenyl succinates, alkoxylated glucose alkenyl succinates and alkoxylated methylglucose alkenyl succinates; silicone emulsifiers; and mixtures thereof. These emulsifiers are characterized by their nonionic nature.

The terms "fatty acid" and "fatty alcohol" mean acids or alcohols having a linear or branched alkyl chain containing from 8 to 30 carbon atoms and preferably from 12 to 24 carbon atoms.

As emulsifiers that may be used in the composition of the invention, mention may be made more particularly of fatty acid esters of polyols, including those comprising at least one oxyethylene unit, and fatty acid esters of sorbitol.

1. Among the fatty acid esters of polyols, including those comprising at least one oxyethylene unit, and the fatty alkyl ethers of polyols, mention may be made especially of:

glyceryl esters, which may be glyceryl, diglyceryl or polyglyceryl monoalkyl, dialkyl or polyalkyl esters, such as glyceryl monoisostearate, such as the product sold under the name Peceol Isostearique (INCI name: glyceryl isostearate) by the company Gattefosse; polyglycerolated (4 mol) isostearate (INCI name: Polyglyceryl-4 isostearate) sold under the name Isolan GI34 by the company Goldschmidt, diglyceryl isostearate, sold by the company Solvay; glyceryl laurate comprising 2 glycerol units, sold by the company Solvay (INCI name: Polyglyceryl-2 laurate), polyglycerolated (10 mol) monoisostearate, sold under the name Nikkol Decaglyn 1-IS by the company Nihon Surfactant (INCI name: Polyglyceryl-10 isostearate), and polyglyceryl-2 diisostearate sold under the name Dermol DGDIS by the company Alzo (INCI name: Polyglyceryl-2 diisostearate).

polyethylene glycol esters (or PEG esters), which are esters formed from 1 to 200 ethylene oxide units and from at least one fatty acid chain containing from 8 to 30 and preferably from 12 to 22 carbon atoms. The fatty chain of the esters may especially be an isostearate chain. Examples of polyethylene glycol esters that may be mentioned include oxyethylenated stearic acid esters such as PEG-20 stearate sold under the name Myrj 49 by the company Uniqema, and oxyethylenated isostearic acid esters such as PEG-8 isostearate, for instance the product sold under the name Prisorine 3644 by the company Uniqema.

2. Among the fatty acid esters of sorbitol, including those comprising at least one oxyethylene unit, mention may be made of $C_8$-$C_{30}$ and preferably $C_{12}$-$C_{22}$ fatty acid esters of sorbitan and oxyethylenated $C_8$-$C_{30}$ and preferably $C_{12}$-$C_{22}$ fatty acid esters of sorbitan. The oxyethylenated esters generally comprise from 1 to 200 ethylene glycol units and preferably from 2 to 40 ethylene oxide (EO) units.

Examples of such emulsifiers that may be mentioned include sorbitan oleate, sold under the name Span 80 by the company Uniqema, oxyethylenated (20 EO) sorbitan monooleate (INCI name: Polysorbate 80) sold by the company Uniqema under the name Tween 80, sorbitan isostearate (INCI name: sorbitan isostearate) sold under the name Nikkol SI 10RV by the company Nikko, or the product sold under the name Arlacel 987 by the company Uniqema. Mention may also be made of the sorbitan laurate sold under the name Span 20 by the company Uniqema.

3. Silicone emulsifiers that may be mentioned include dimethicone copolyols, such as the mixture of cyclomethicone and of dimethicone copolyol sold under the name DC 5225 C by the company Dow Corning, and alkyl dimethicone copolyols, such as the lauryl methicone copolyol sold under the name Dow Corning 5200 Formulation Aid by the company Dow Corning and the cetyldimethicone copolyol sold under the name Abil EM 90 by the company Goldschmidt, or the polyglyceryl-4 isostearate/cetyl dimethicone copolyol/hexyl laurate mixture sold under the name Abil WE 90 by the company Goldschmidt.

The composition according to the invention may contain one or more of these emulsifiers.

According to one preferred embodiment of the invention, the emulsifier is chosen from glyceryl esters, polyethylene glycol esters, and mixtures thereof, and more particularly from:

glyceryl isostearate, sold under the name Peceol Isostearique by the company Gattefosse;

polyethylene glycol esters of stearic acid such as PEG-20 stearate.

Aqueous Phase

Advantageously, the amphiphilic polymer is introduced into the aqueous phase of the emulsion. In addition, the aqueous phase contains water and optionally one or more water-miscible or at least partially water-miscible compounds, for instance polyols; $C_2$ to $C_8$ lower monoalcohols, such as ethanol and isopropanol. The term "room temperature" should be understood as meaning a temperature of about 25° C., at normal atmospheric pressure (760 mmHg).

The term "polyol" should be understood as meaning any organic molecule comprising at least two free hydroxyl groups. Examples of polyols that may be mentioned include glycols, for instance butylene glycol, propylene glycol, and isoprene glycol, glycerol and polyethylene glycols, for instance PEG-8, sorbitol and sugars, for instance glucose.

The aqueous phase may also comprise any common water-soluble or water-dispersible additive as mentioned below.

The aqueous phase may represent from 60% to 98% by weight, preferably from 65% to 95% by weight, better still from 70% to 90% by weight and even better still from 70% to 85% by weight relative to the total weight of the composition.

The water-miscible compound(s), such as lower polyols and alcohols, may be present in an amount ranging from 0 to 30%, especially from 0.1% to 30% and better still in an amount ranging from 1% to 20%, relative to the total weight of the composition.

Oily Phase

The nature of the oily phase of the emulsion according to the invention is not critical. The oily phase is a fatty phase containing at least one fatty substance chosen from volatile or non-volatile oils that are liquid at room temperature (20-25° C.), gums and pasty fatty substances of plant, mineral or synthetic origin, and mixtures thereof. These fatty substances are physiologically acceptable.

The oily phase may also comprise any common liposoluble or lipodispersible additive as mentioned below.

The oily phase contains at least one oil, more particularly at least one cosmetic oil. The term "oil" means a fatty substance that is liquid at room temperature (25° C.).

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;

synthetic esters and ethers, especially of fatty acids, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, isohexadecane, isododecane, and hydrogenated polyisobutene such as Parleam® oil;

partially hydrocarbon-based and/or silicone-based fluoro oils, for instance those described in document JP-A-2 295 912;

silicone oils, for instance volatile or non-volatile polymethylsiloxanes (PDMSs) containing a linear or cyclic silicone chain, which are liquid or pasty at room temperature, especially volatile silicone oils, in particular cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes;

mixtures thereof.

According to one preferred embodiment, the composition of the invention comprises at least one oil chosen from silicone oils, linear or branched hydrocarbons, synthetic ethers and esters, and mixtures thereof and is especially chosen from volatile silicone oils and branched hydrocarbons, for instance Parleam® oil, and mixtures thereof.

The amount of oily phase in the composition of the invention is less than 40% of the total weight of the emulsion and may range, for example, from 2% to 40% by weight, preferably from 5% to 35% by weight, better still from 10% to 30% by weight and even better still from 15% to 30% by weight relative to the total weight of the composition. As indicated above, this amount of oily phase does not comprise the amount of emulsifier.

Additives

The compositions of the invention may also contain one or more adjuvants, including those that are common in cosmetics or dermatology. Adjuvants that may be mentioned include gelling agents, active agents, preserving agents, antioxidants, fragrances, solvents, salts, fillers, sunscreens (=UV-screening agents), dyestuffs, basic agents (triethanolamine, diethanolamine or sodium hydroxide) or acidic agents (citric acid), and also lipid vesicles or any other type of vector (nanocapsules, microcapsules, etc.), and mixtures thereof. These adjuvants are used in the usual proportions in the cosmetics field, for example from 0.01% to 30% of the total weight of the composition, and, depending on their nature, they are introduced into the aqueous phase of the composition or into the oily phase, or alternatively into vesicles or any other type of vector. These adjuvants and the concentrations thereof must be such that they do not modify the desired property for the emulsion of the invention.

Depending on the desired viscosity of the composition according to the invention, it is possible to incorporate therein one or more hydrophilic or lipophilic gelling agents. Examples of hydrophilic gelling agents that may be mentioned include modified or unmodified carboxyvinyl polymers, such as the products sold under the names Carbopol (INCI name: carbomer) and Pemulen (INCI name: Acrylates/C10-30 alkyl acrylate crosspolymer) by the company Noveon; polyacrylamides; optionally crosslinked and/or neutralized 2-acrylamido-2-methylpropane sulfonic acid polymers and copolymers, for instance the poly(2-acrylamido-2-methylpropanesulfonic acid) sold by the company Clariant under the name "Hostacerin AMPS" (INCI name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance guar gum, alginates and modified or unmodified celluloses; and mixtures thereof. When they are present, these gelling agents must be introduced in an amount such that they do not modify the properties of the composition according to the invention. Lipophilic gelling agents that may especially be mentioned include modified clays such as modified magnesium silicate (Bentone Gel VS38 from Rheox), or hectorite modified with distearyldimethylammonium chloride (INCI name: Disteardimonium hectorite) sold under the name Bentone 38 CE by the company Rheox.

As fillers that may be used in the composition of the invention, examples that may be mentioned include the pigments such as titanium oxide, zinc oxide or iron oxide and organic pigments; kaolin; silica; talc; boron nitride; organic spherical powders, fibres; and mixtures thereof. Examples of organic spherical powders that may be mentioned include polyamide powders and especially Nylon® powders such as Nylon-1 or Polyamide 12, sold under the name Orgasol by the company Atochem; polyethylene powders; Teflon®; microspheres based on acrylic copolymers, such as those made of ethylene glycol dimethacrylate/lauryl methacrylate copolymer, sold by the company Dow Corning under the name Polytrap; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; polymethyl methacrylate microspheres, sold under the name Microsphere M-100 by the company Matsumoto or under the name Covabead LH85 by the company Wackherr; ethylene acrylate copolymer powders, such as those sold under the name Flobeads by the company Sumitomo Seika Chemicals; powders of natural organic materials such as starch powders, especially of maize starch, wheat starch or rice starch, which may or may not be crosslinked, such as the starch powders crosslinked with octenyl succinate anhydride, sold under the name Dry-Flo by the company National Starch. Examples of fibres that may be mentioned include polyamide fibres, especially such as Nylon 6 (or Polyamide 6) (INCI name: Nylon 6) fibres, Nylon 6,6 (or Polyamide 66) (INCI name: Nylon 66) fibres, or such as poly-p-phenyleneterephthamide fibres; and mixtures thereof. These fillers may be present in amounts ranging from 0 to 20% by weight and preferably from 0.5% to 10% by weight relative to the total weight of the composition.

As active agents that may be used in the composition of the invention, examples that may be mentioned include moisturizers such as protein hydrolysates; sodium hyaluronate; polyols, for instance glycerol, glycols, for instance polyethylene glycols, and sugar derivatives; anti-inflammatory agents; procyannidol oligomers; vitamins, for instance vitamin A (retinol), vitamin E (tocopherol), vitamin K, vitamin C (ascorbic acid), vitamin B5 (panthenol), vitamin B3 or PP (niacinamide), derivatives of these vitamins (especially esters) and mixtures thereof; keratolytic agents and/or desquamating agents, such as salicylic acid and its derivatives, α-hydroxy acids, for instance lactic acid and glycolic acid and derivatives thereof, and ascorbic acid and its derivatives; urea; caffeine; depigmenting agents such as kojic acid, hydroquinone and caffeic acid; salicylic acid and its derivatives; retinoids such as carotenoids and vitamin A derivatives; hydrocortisone; melatonin; algal extracts, fungal extracts, plant extracts, yeast extracts or bacterial extracts; steroids; antibacterial active agents, for instance 2,4,4'-trichloro-2'-hydroxy-diphenyl ether (or triclosan), 3,4, 4'-trichlorocarbanilide (or triclocarban) and the acids indicated above, and especially salicylic acid and its derivatives; enzymes; flavonoids; tensioning agents such as synthetic polymers, plant proteins, polysaccharides of plant origin optionally in the form of microgels, starches, wax dispersions, mixed silicates and colloidal particles of mineral fillers; ceramides; anti-inflammatory agents; calmatives; mattifying agents; agents for preventing hair loss and/or for promoting regrowth of the hair; anti-wrinkle agents; essential oils; and mixtures thereof; and any active agent that is suitable for the final aim of the composition.

The UV-screening agents may be organic or mineral (or physical UV sunblocks). They may be present in an active-material amount ranging from 0.01% to 20% by weight of active material, preferably from 0.1% to 15% by weight and better still 0.2% to 10% by weight relative to the total weight of the composition.

As examples of UV-A-active and/or UV-B-active organic screening agents that may be added to the composition of the invention, mention may be made of the anthranilates; cinnamic derivatives; dibenzoylmethane derivatives; salicylic derivatives, camphor derivatives; triazine derivatives such as those described in patent applications U.S. Pat. No. 4,367,390, EP 863 145, EP 517 104, EP 570 838, EP 796 851, EP 775 698, EP 878 469 and EP 933 376; benzophenone derivatives; β,β'-diphenylacrylate derivatives; benzotriazole derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenyl-benzotriazole) derivatives as described in applications U.S. Pat. Nos. 5,237,071, 5,166,355, GB 2 303 549, DE 197 26 184 and EP 893 119; screening polymers and screening silicones such as those described in particular in application WO 93/04665; α-alkylstyrene-based dimers such as those described in patent application DE 198 55 649.

Mention may be made more particularly of the following UV-screening agents, designated below under their INCI name:
Para-Aminobenzoic Acid Derivatives:
PABA,
Ethyl PABA,
Ethyl dihydroxypropyl PABA,
Ethylhexyl dimethyl PABA sold in particular under the name Escalol 507 by ISP,
Glyceryl PABA,
PEG-25 PABA sold under the name Uvinul P25 by BASF,
Salicylic Derivatives:
Homosalate sold under the name Eusolex HMS by Rona/EM Industries,
Ethylhexyl salicylate sold under the name Neo Heliopan OS by Haarmann and Reimer,
Dipropylene glycol salicylate sold under the name Dipsal by Scher,
TEA salicylate, sold under the name Neo Heliopan TS by Haarmann and Reimer,
Dibenzoylmethane Derivatives:
Butylmethoxydibenzoylmethane sold in particular under the trade name Parsol 1789 by Hoffmann LaRoche, Isopropyldibenzoylmethane,
Cinnamic Derivatives:
Ethylhexyl methoxycinnamate sold in particular under the trade name Parsol MCX by Hoffmann LaRoche,
Isopropyl methoxycinnamate,
Isoamyl methoxycinnamate sold under the trade name Neo Heliopan E 1000 by Haarmann and Reimer,
Cinoxate,
DEA methoxycinnamate,
Diisopropyl methylcinnamate,
Glyceryl ethylhexanoate dimethoxycinnamate,
β,β'-Diphenylacrylate Derivatives:
Octocrylene sold in particular under the trade name Uvinul N539 by BASF,
Etocrylene, sold in particular under the trade name Uvinul N35 by BASF,
Benzophenone Derivatives:
Benzophenone-1 sold under the trade name Uvinul 400 by BASF,
Benzophenone-2 sold under the trade name Uvinul D50 by BASF,
Benzophenone-3 or Oxybenzone, sold under the trade name Uvinul M40 by BASF,
Benzophenone-4 sold under the trade name Uvinul MS40 by BASF,
Benzophenone-5,
Benzophenone-6 sold under the trade name Helisorb 11 by Norquay,
Benzophenone-8 sold under the trade name Spectra-Sorb UV-24 by American Cyanamid,
Benzophenone-9 sold under the trade name Uvinul DS-49 by BASF,
Benzophenone-12,
Benzylidenecamphor Derivatives:
3-Benzylidenecamphor manufactured under the name Mexoryl SD by Chimex,
4-Methylbenzylidenecamphor sold under the name Eusolex 6300 by Merck,
Benzylidenecamphorsulfonic acid manufactured under the name Mexoryl SL by Chimex,
Camphorbenzalkonium methosulfate manufactured under the name Mexoryl SO by Chimex,
Terephthalylidenedicamphorsulfonic acid manufactured under the name Mexoryl SX by Chimex,
Polyacrylamidomethylbenzylidenecamphor manufactured under the name Mexoryl SW by Chimex,
Phenylbenzimidazole Derivatives:
Phenylbenzimidazolesulfonic acid sold in particular under the trade name Eusolex 232 by Merck,
Benzimidazilate sold under the trade name Neo Heliopan AP by Haarmann and Reimer, Triazine Derivatives:
Anisotriazine sold under the trade name Tinosorb S by Ciba Geigy,
Ethylhexyl triazone sold in particular under the trade name Uvinul T150 by BASF,
Diethylhexyl butamido triazone sold under the trade name Uvasorb HEB by Sigma 3V,
Phenylbenzotriazole Derivatives:
Drometrizole trisiloxane sold under the name Silatrizole by Rhodia Chimie,
Methylenebis-benzotriazolyl-tetramethylbutylphenol, sold in solid form under the trade name Mixxim BB/100 by Fairmount Chemical or in micronized form in aqueous dispersion under the trade name Tinosorb M by Ciba Specialty Chemicals,
Anthranilic Derivatives:
Menthyl anthranilate sold under the trade name Neo Heliopan MA by Haarmann and Reimer,
Imidazoline Derivatives:
Ethylhexyl Dimethoxybenzylidene Dioxoimidazoline propionate,
Benzalmalonate Derivatives:
Polyorganosiloxane with benzalmalonate functions sold under the trade name Parsol SLX by Hoffmann LaRoche,
and mixtures of these screening agents.

The organic UV-screening agents that are more particularly preferred are chosen from the following compounds:
Ethylhexyl salicylate,
Butylmethoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
4-Methylbenzylidenecamphor,
Benzimidazilate,
Anisotriazine,
Ethylhexyl triazone,
Diethylhexyl butamido triazone,
Methylenebis-benzotriazolyl-tetramethylbutylphenol,
Drometrizole trisiloxane,
and mixtures thereof.

The total amount of organic UV-screening agents in the compositions according to the invention may range, for example, from 0.1% to 20% by weight relative to the total weight of the composition, preferably ranging from 0.2% to 15% by weight relative to the total weight of the composition.

As physical sunblocks that may be added to the composition of the invention, examples that may be mentioned include pigments and nanopigments of coated or uncoated metal oxides, especially titanium oxide, iron oxide, zirconium oxide, zinc oxide or cerium oxide, and mixtures thereof, these oxides possibly being in the form of optionally coated microparticles or nanoparticles (nanopigments).

The compositions of the invention are prepared according to the usual processes for the preparation of O/W emulsions. The amphiphilic AMPS copolymer is dissolved with stirring in the aqueous phase, preferably at room temperature (25° C.), and the emulsion is prepared by introducing the oily phase into the aqueous phase with stirring.

The compositions according to the invention may be in any form including, for example, in any of the galenical forms of O/W emulsions, for example in the form of a serum, a milk or a cream, and they are prepared according to the usual methods. The compositions that are the subject of the invention are intended for topical application and can especially constitute a dermatological or cosmetic composition intended, for example, for caring for (anti-wrinkle, anti-ageing, moisturizing, antisun, etc.), treating, cleansing and making up keratin materials, and especially human skin, lips, hair, eyelashes and nails.

According to one preferred embodiment of the invention, the composition constitutes a cosmetic composition and is intended for topical application to the skin.

Thus, a subject of the invention is also the cosmetic use of a cosmetic composition as defined above, for caring for, removing makeup from and/or cleansing the skin, the lips and/or the hair.

Finally, a subject of the invention is a cosmetic process for treating the skin, including the scalp, the hair and/or the lips, wherein a cosmetic composition as defined above is applied to the skin, the hair and/or the lips.

The examples that follow will allow the invention to be understood more clearly, without, however, being limiting in nature. Unless otherwise mentioned, the amounts indicated are percentages by weight.

V) EXAMPLES

General Procedure for Preparing the Emulsions:
The amphiphilic copolymers of the invention, provided in powder form, are dissolved in water for 30 minutes with stirring at 25° C.; the solution obtained is macroscopically homogeneous. The emulsion is prepared by slow introduction of the oily phase into the aqueous phase with stirring using a Moritz homogenizer at a stirring speed of 4000 rpm for:
 15 minutes for the emulsions comprising drops greater than 1 µm in size,
 5 minutes, and the emulsion is then refined using a Rannie homogenizer at a pressure equal to 500 bar (3 runs), for the emulsions comprising drops less than 1 µm in size.

The drop size of the micron-sized emulsions is measured using a Hydro 2000 S/G laser granulometer (Malvern) on the basis of the mean surface diameter D(3,2), and the drop size of the submicron-based emulsions is measured using a BI-90 size analyser (Brookhaven Instrument).

Example 1 According to the Invention

Moisturizing Body Fluid

| Phase A: | |
|---|---:|
| Distilled water | 83.175% |
| Preserving agent | 1% |
| Triethanolamine | 0.002% |
| Copolymer of AMPS and of Genapol T-080 methacrylate (7.35 mol %) (Aristoflex SNC) | 0.4% |
| Phase B: | |
| Parleam oil | 9% |
| Cyclohexadimethylsiloxane | 6% |
| Glyceryl isostearate (Peceol isostearique from Gattefosse) | 0.45 |

Phase B was added to phase A with very vigorous stirring, at room temperature. The size of the drops was about 3 µm. Its viscosity, measured using a Rheomat 180 viscometer at 25° C. at a spin speed of the No. 3 spindle of 200 rpm, was 0.068 Pa·s. This emulsion was stable after 2 months at 55° C.

This example shows that the combination of a polymer of the invention and of glyceryl isostearate, in a concentration mass ratio equal to 1, makes it possible to stabilize the emulsion. The low content of polymer and of emulsifier makes it possible to obtain an emulsion that shows good harmlessness with respect to the skin.

Comparative Example 2

| Phase A: | |
|---|---|
| Distilled water | 83.585% |
| Preserving agent | 1% |
| Triethanolamine | 0.002% |
| Copolymer of AMPS and of Genapol T-080 methacrylate (7.35 mol %) (Aristoflex SNC) | 0.4% |
| Phase B: | |
| Parleam oil | 9% |
| Cyclohexadimethylsiloxane | 6% |

Phase B was added to phase A with very vigorous stirring, at room temperature. The mean size of the drops was about 8 μm. The viscosity, measured using a Rheomat 180 viscometer at 25° C. at a spin speed of the No. 2 spindle of 200 rpm, was 0.061 Pa·s. The emulsion destabilized after 5 days at 55° C.

This comparative example of Example 1 shows that the presence of a liquid nonionic emulsifier is necessary to obtain a stable emulsion.

Comparative Example 3

| Phase A: | |
|---|---|
| Distilled water | 83.385% |
| Preserving agent | 1% |
| Triethanolamine | 0.001% |
| Copolymer of AMPS and of Genapol T-080 methacrylate (7.35 mol %) (Aristoflex SNC) | 0.4% |
| Phase B: | |
| Parleam oil | 9% |
| Cyclohexadimethylsiloxane | 6% |
| Glyceryl isostearate (Peceol isostearique from Gattefosse) | 0.2% |

Phase B was added to phase A with very vigorous stirring, at room temperature. The mean size of the drops obtained was equal to 5 μm. The viscosity, measured using a Rheomat 180 viscometer at 25° C. at a spin speed of the No. 2 spindle of 200 rpm, was 0.060 Pa·s. The emulsion became coarse after 2 months at 55° C., with globules about 15 μm in size.

This comparative example of Example 1 shows that a polymer/emulsifier weight ratio equal to 2 is insufficient to stabilize the emulsion.

Comparative Example 4

| Phase A: | |
|---|---|
| Distilled water | 82.975% |
| Preserving agent | 1% |
| Triethanolamine | 0.002% |
| Copolymer of AMPS and of Genapol LA-070 methacrylate (8.5 mol %) (Aristoflex LNC) | 0.5% |
| Phase B: | |
| Parleam oil | 9% |
| Cyclohexadimethylsiloxane | 68% |
| Glyceryl isostearate (Peceol isostearique from Gattefosse) | 0.5% |

Phase B was added to phase A with very vigorous stirring. The mean size of the drops obtained was about 5 μm. Its viscosity, measured using a Rheomat 180 viscometer at 25° C. at a spin speed of the No. 2 spindle of 200 rpm, was 0.060 Pa·s. The emulsion became coarse after 2 months at 55° C., with the appearance of globules about 20 μm in size. This comparative example shows that the combination of a polymer not forming part of the invention, in which R2 in formula (II) comprises 12 to 14 carbon atoms, as described in patent application FR-2 853 527, with a lipophilic emulsifier in a mass ratio equal to 1 does not allow the emulsion to be stabilized, for a low content of emulsifying polymer (amount of polymer ≤0.6%).

Example 5 According to the Invention

Body Milk

| Phase A: | |
|---|---|
| Distilled water | 77.996% |
| Preserving agent | 1% |
| Triethanolamine | 0.004% |
| Copolymer of AMPS and of Genapol T-080 methacrylate (7.35 mol %) (Aristoflex SNC) | 0.5% |
| Phase B: | |
| Parleam oil | 12% |
| Cyclohexadimethylsiloxane | 8% |
| Glyceryl isostearate (Peceol isostearique from Gattefosse) | 0.5% |

Procedure: phase B was added to phase A with vigorous stirring.

A fluid milk that was stable for at least 2 months, and whose drop size was about 2 μm, was obtained. Its viscosity, measured using a Rheomat 180 viscometer at 25° C. at a spin speed of the No. 2 spindle of 200 rpm, was 0.123 Pa·s.

This example shows that the combination of a polymer of the invention and of glyceryl isostearate in the ratio defined according to the invention allows a stable emulsion to be obtained.

Comparative Example 6

| Phase A: | |
|---|---|
| Distilled water | 77.995% |
| Preserving agent | 1% |
| Triethanolamine | 0.005% |
| Copolymer of AMPS and of Genapol T-080 methacrylate (7.35 mol %) (Aristoflex SNC) | 0.5% |

Phase B:

| | |
|---|---|
| Parleam oil | 12% |
| Cyclohexadimethylsiloxane | 8% |
| Stearic acid | 0.5% |

Procedure: phase B, preheated to 65° C., was added with vigorous stirring to phase A, also at 65° C. A thick milk whose drop size was about 5 µm was obtained. Its pH was equal to 7.1 and its viscosity, measured using a Rheomat 180 viscometer at 25° C. at a spin speed of the No. 3 spindle of 200 rpm, was 0.069 Pa·s. After 48 hours at 4° C., microscopic destabilization (coalescence) was observed: the size of the drops increased from 5 µm to 25 µm, which shows the instability of the emulsion.

This comparative example shows that it is essential for the emulsifier to be nonionic in order to obtain a stable emulsion, and that an ionic emulsifier that is solid at 45° C., such as stearic acid, does not ensure the stability of an oil-in-water emulsion based on the polymers of the invention.

Example 7 According to the Invention

Facial Cream

| Phase A: | |
|---|---|
| Distilled water | 59.997% |
| Preserving agent | 1% |
| Triethanolamine | 0.003% |
| Copolymer of AMPS and of Genapol T-080 methacrylate (7.35 mol %) | 0.5% |
| Phase B: | |
| Parleam oil | 22.8% |
| Cyclohexadimethylsiloxane | 15.2% |
| Glyceryl isostearate (Peceol isostearique from Gattefosse) | 0.5% |

Procedure: phase B was added with very vigorous stirring to phase A, at room temperature. A cream that was stable for at least 2 months was obtained; the drop size was about 2 µm. Its viscosity, measured using a Rheomat 180 viscometer at 25° C. at a spin speed of the No. 3 spindle of 200 rpm, was 0.21 Pa·s.

Comparative Example 8

| Phase A: | |
|---|---|
| Distilled water | 78% |
| Preserving agent | 1% |
| Copolymer of AMPS and of Genapol T-080 methacrylate (7.35 mol %) (Aristoflex SNC) | 0.5% |
| Phase B: | |
| Parleam oil | 12% |
| Cyclohexadimethylsiloxane | 8% |
| Stearic acid | 0.5% |

Procedure: phase B, preheated to 65° C., was added with vigorous stirring to phase A, also at 65° C. A thick milk whose drop size was about 5 µm was obtained. After 12 hours at 4° C., macroscopic destabilization (creaming) was observed.

This comparative example shows that it is necessary for the emulsifier used to be nonionic in order to obtain a stable emulsion, and that an ionic emulsifier such as disodium stearoyl glutamate does not ensure the stability of an oil-in-water emulsion based on the polymers of the invention.

Example 9 According to the Invention

Body Milk

| Phase A: | |
|---|---|
| Distilled water | 77.996% |
| Preserving agent | 1% |
| Triethanolamine | 0.004% |
| Copolymer of AMPS and of Genapol T-080 methacrylate (7.35 mol %) (Aristoflex SNC) | 0.5% |
| Phase B: | |
| Parleam oil | 12% |
| Cyclohexadimethylsiloxane | 8% |
| PEG-20 stearate | 0.5% |

Procedure: phase B was added with very vigorous stirring to phase A.

A fluid milk that was stable for at least 1 month, with a drop size of 3 µm, was obtained. Its viscosity, measured using a Rheomat 180 viscometer at 25° C. at a spin speed of the No. 2 spindle of 200 rpm, was 0.096 Pa·s.

This example shows that the combination of a polymer of the invention and of PEG-20 stearate (melting point of 28° C.) makes it possible to stabilize the emulsion.

Comparative Example 10

| Phase A: | |
|---|---|
| Distilled water | 82.955% |
| Preserving agent | 1% |
| Copolymer of AMPS and of Genapol T-080 methacrylate (7.35 mol %) (Aristoflex SNC) | 1% |
| Phase B: | |
| Parleam oil | 9% |
| Cyclohexadimethylsiloxane | 6% |

Procedure: phase B, at room temperature, was added with vigorous stirring to phase A. A very elastic gelled cream with a drop size equal to 3 µm was obtained. This gelled cream was not cosmetic on account of its elasticity and its poor uptake by finger.

This comparative example shows that it is necessary to consider a low content of emulsifying polymer in order to obtain a pleasant cosmetic texture that is easy to apply.

The above written description of the invention provides a manner and process of making and using it such that any person skilled in this art is enabled to make and use the same, this enablement being provided in particular for the subject matter of the appended claims, which make up a part of the original description and including a composition preferably suitable for topical application, in the form of an oil-in-water emulsion comprising an oily phase dispersed in an aqueous phase, wherein it contains (a) one or more nonionic emulsifiers with a melting point of less than 45° C., and (b) one or more non-crosslinked polymers comprising (A) 80 mol % to 99 mol % of 2-acrylamido-2-methylpropanesulfonic acid units of formula (I):

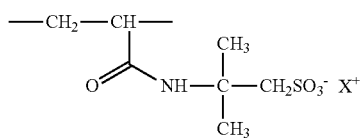

in which $X^+$ is a proton, an alkali metal cation, an alkaline-earth metal cation or an ammonium ion;
and (B) 1 mol % to 20 mol % of units of formula (II) below:

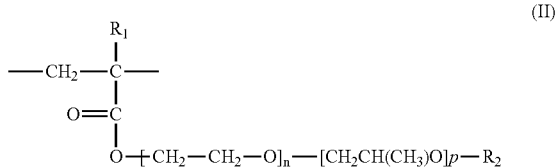

in which n and p, independently of each other, denote a number of moles ranging from 0 to 30, with the proviso that n+p is less than or equal to 30; $R_1$ denotes a hydrogen atom or a linear or branched $C_1$-$C_6$ alkyl radical, and $R_2$ denotes a linear or branched alkyl radical containing from 16 to 30 carbon atoms,
the amount of polymer(s) (b) being less than or equal to 0.6% by weight relative to the total weight of the composition, and the weight ratio between the amount of polymer(s) (b) and the amount of emulsifier(s) (a) ranging from 0.7 to 1.3,
and in that the oily phase is present in an amount of less than 40% by weight relative to the total weight of the composition.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition which is suitable for topical application to a keratin material and in the form of an oil-in-water emulsion, wherein the composition comprises an oily phase dispersed in an aqueous phase and:
   (a) from 0.15 to 0.65% by weight of glyceryl isostearate and optionally one or more additional emulsifiers; and
   (b) from 0.1 to 0.6% by weight of ammonium acryloyldimethyltaurate/Steareth-8 methacrylate copolymer,
   wherein the weight ratio of the amount of ammonium acryloyldimethyltaurate/Steareth-8 methacrylate copolymer to the amount of glyceryl isostearate ranges from 0.9 to 1.1, and
   wherein the oily phase is present in an amount greater than zero but less than 40% by weight relative to the total weight of the composition.

2. The composition according to claim 1, wherein the amount of ammonium acryloyldimethyltaurate/Steareth-8 methacrylate copolymer is 0,05% to 0.5% by weight.

3. A method for caring for, removing makeup from and/or cleansing the skin, the lips and/or the hair, comprising applying the composition of claim 1 to the skin, the lips and/or the hair.

4. The composition according to claim 1, which is a stable emulsion for 2 months at 55° C. defined by no macroscopic change in color, odor, and/or viscosity, no variation in pH and no change in microscopic appearance.

* * * * *